(12) United States Patent
Kobayashi et al.

(10) Patent No.: US 7,718,396 B2
(45) Date of Patent: May 18, 2010

(54) INDUCIBLE HIGH EXPRESSION SYSTEM

(75) Inventors: Michihiko Kobayashi, 97-306, Shimobaba-cho, Jyodoji, Sakyo-ku, Kyoto-shi, Kyoto 606-8413 (JP); Yoshiteru Hashimoto, Tsukuba (JP); Hiroki Higashibata, Tsukuba (JP)

(73) Assignees: Michihiko Kobayashi, Kyoto-shi (JP); Astellas Pharma Inc., Tokyo (JP)

( * ) Notice: Subject to any disclaimer, the term of this patent is extended or adjusted under 35 U.S.C. 154(b) by 593 days.

(21) Appl. No.: 10/377,803

(22) Filed: Mar. 4, 2003

(65) Prior Publication Data

US 2004/0053273 A1    Mar. 18, 2004

(30) Foreign Application Priority Data

Sep. 5, 2002  (JP)  ............................ 2002-260679

(51) Int. Cl.
*C12N 15/00* (2006.01)
*C07H 21/04* (2006.01)

(52) U.S. Cl. ................ 435/69.1; 435/252.1; 435/320.1; 536/23.1

(58) Field of Classification Search ................ 536/23.1, 536/23.2, 24.1; 435/69.1, 69.2, 370.1
See application file for complete search history.

(56) References Cited

U.S. PATENT DOCUMENTS 5,830,693 A    11/1998    Shimizu et al.

FOREIGN PATENT DOCUMENTS

JP    9-28380    2/1997

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*
H. Komeda, et al., Proc. Natl. Acad. Sci. USA, vol. 93, pp. 10572-10577, "Transcriptional Regulation of the Rhodococcus Rhodochrous J1 nitA Gene Encoding a Nitrilase", Oct. 1996.
M. Kobayashi, et al., The Journal of Biological Chemistry, vol. 267. No. 29, pp. 20746-20751, "Nitrilase From Rhodococcus Rhodochrous J1 Sequencing and Overexpression of the Gene and Identification of an Essential Cysteine Residue", Oct. 15, 1992.

* cited by examiner

*Primary Examiner*—Richard G Hutson
(74) *Attorney, Agent, or Firm*—Oblon, Spivak, McClelland, Maier & Neustadt, L.L.P.

(57) ABSTRACT

The present invention provides a vector containing a DNA construct containing a first promoter that is a nitrilase gene promoter, a multicloning site and a nitrilase transcription regulatory protein gene (particularly preferably a structural gene is ligated into a multicloning site and a second promoter is placed at the upstream of the nitrilase transcription regulatory protein gene), and the like. The present invention affords a high expression system capable of expressing a large amount of useful proteins by actinomycete host represented by actinomycete belonging to the genus *Streptomyces* and the like beneficially used for the production of useful proteins.

33 Claims, 5 Drawing Sheets

Inducible high expression vector

SEQUENCE LISTING

<160> NUMBER OF SEQ ID NOS: 15

<210> SEQ ID NO 1
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
cgacgcgttc cccgcaaaag cggccttt                                      28

<210> SEQ ID NO 2
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
gaagatcttc taaagttttg tcgtcttt                                      28

<210> SEQ ID NO 3
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
cgggatccac ggctaccctg aaaagagc                                      28

<210> SEQ ID NO 4
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
ggactagtcc gggctcttcc tacgaaac                                      28

<210> SEQ ID NO 5
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
cgggatccgc gaactccctt atgcgggt                                      28

<210> SEQ ID NO 6
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
gaagatctgt tgcttgtgtt tggcagga                                      28

<210> SEQ ID NO 7
<211> LENGTH: 28

<212> TYPE: DNA
<213> ORGANISM: ARTIFICIAL SEQUENCE
<220> FEATURE:
<223> OTHER INFORMATION: SYNTHETIC DNA

<400> SEQUENCE: 7
cgctcgaggc gaactccctt atgcgggt                                      28

<210> SEQ ID NO 8
<211> LENGTH: 56
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
cgatgcatac tagtacgcgt agatctgttg cttgtgtttg gcaggacagt acgagg       56

<210> SEQ ID NO 9
<211> LENGTH: 34
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
aactgcagtg tacatccccg caaaagcggc cttt                               34

<210> SEQ ID NO 10
<211> LENGTH: 29
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
ccgctcgagt ctaaagtttt gtcgtctttt                                    29

<210> SEQ ID NO 11
<211> LENGTH: 29
<212> TYPE: DNA
<213> ORGANISM: ARTIFICIAL SEQUENCE
<220> FEATURE:
<223> OTHER INFORMATION: SYNTHETIC DNA

<400> SEQUENCE: 11
caacaagatc tgaattcgag ctcggtacc                                     29

<210> SEQ ID NO 12
<211> LENGTH: 29
<212> TYPE: DNA
<213> ORGANISM: ARTIFICIAL SEQUENCE
<220> FEATURE:
<223> OTHER INFORMATION: SYNTHETIC DNA

<400> SEQUENCE: 12
cgagaagatc taagcttgca tgcctgcag                                     29

<210> SEQ ID NO 13
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 13

-continued

```
gccaaagctt agcaacggag gtacgg                                       26

<210> SEQ ID NO 14
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 14
cgctgcagtc agatggaggc tgtcg                                        25

<210> SEQ ID NO 15
<211> LENGTH: 118
<212> TYPE: DNA
<213> ORGANISM: ARTIFICIAL SEQUENCE
<220> FEATURE:
<223> OTHER INFORMATION: SYNTHETIC DNA

<400> SEQUENCE: 15
gcgaactccc ttatgcgggt ggcgcagaat gccaggaccc ttgtcattcc acgtcaattc    60
atgcgccttt tcacctcgta ctgtcctgcc aaacacaagc aacggaggta cggacatg    118
```

INDUCIBLE HIGH EXPRESSION SYSTEM

TECHNICAL FIELD OF THE INVENTION

The present invention relates to a novel expression system of a structural gene. More particularly, this invention relates to the construction of an inducible high expression vector utilizing a nitrilase expression control system.

BACKGROUND OF THE INVENTION

The genus *Streptomyces* has been widely employed for industrial use as antibiotics-producing bacteria and has become an extremely important bacterial group for applied microbiology of today. In view of the significance of the production of useful substances by the genus *Streptomyces*, development of an inducible large-scale expression system capable of controlling the expression in actinomycete is desired. The present inventors have already obtained an inducible expression system for a protein (nitrilase) derived from *Rhodococcus rhodochrous* J1 (FERM BP-1478), which is one species of the actinomycete (JP-A-9-28380, and Proceedings of the National Academy of Sciences USA, October 1996, No. 93, pp. 10572-10577). This expression system expresses nitrilase (enzyme decomposing nitrile into acid and ammonia) in a large amount of not less than 35% of the total soluble protein in a cell-free extract, when isovaleronitrile is added to a medium as an inducer. In other words, an inducible promoter with an extremely potent transcription activity is involved in this expression system.

However, this finding concerns only a part of the actinomycete: *Rhodococcus rhodochrous* J1 strain, and there is no report or even a suggestion to date if a similar expression system can be utilized for actinomycetes belonging to other genera, particularly the genus *Streptomyces*, whose importance has been pointed out for the above-mentioned reasons.

SUMMARY OF THE INVENTION

The present invention aims at analyzing the function, in the genus *Streptomyces*, of the inducible expression control system of protein (nitrilase) devised for the genus *Rhodococcus*, and, based on which finding, developing a novel inducible high expression vector. A final object of the present invention is application of this expression system to a large-scale production of various proteins and physiologically active substances.

In an attempt to achieve the above-mentioned object, the present inventors have first studied if the inducible high expression control system of the genus *Rhodococcus* functions for other actinomycetes, such as the genus *Streptomyces*. As a result, the system has been found to be functional even only with extremely simple genetic regions of nitrilase gene promoter, nitrilase structural gene and nitrilase transcription regulatory protein gene. Moreover, by placing a second promoter at the upstream of the nitrilase transcription regulatory protein gene, the present invention has been completed with successful and remarkable promotion of the expression of the objective structural gene (e.g., nitrilase) by nitrilase transcription regulatory protein, as well as promotion of the expression of the nitrilase transcription regulatory protein itself. Accordingly, the present invention provides the following.

(1) A DNA construct comprising a first promoter that is a nitrilase gene promoter, a nitrilase structural gene, a nitrilase transcription regulatory protein gene and a second promoter placed at the upstream of the nitrilase transcription regulatory protein gene.

(2) A DNA construct comprising a first promoter that is a nitrilase gene promoter, a multicloning site and a nitrilase transcription regulatory protein gene.

(3) The DNA construct of the above-mentioned (2), further comprising a second promoter at the upstream of the nitrilase transcription regulatory protein gene.

(4) The DNA construct of the above-mentioned (2) or (3), wherein a structural gene is ligated into the multicloning site.

(5) A DNA construct comprising a first promoter that is a nitrilase gene promoter, a cloning site, a nitrilase transcription regulatory protein gene and a second promoter placed at the upstream of the nitrilase transcription regulatory protein gene.

(6) The DNA construct of any of the above-mentioned (1), (3) and (5), wherein the second promoter is a nitrilase gene promoter.

(7) The DNA construct of any of the above-mentioned (1) to (6), is further comprising a terminator region at the upstream of the first promoter and/or the second promoter.

(8) A vector functionally comprising both the DNA construct of any of the above-mentioned (1) to (7) and a DNA involved in a regulatory function of intracellular autonomous replication of actinomycete.

(9) The vector of the above-mentioned (8), further functionally comprising a DNA involved in a regulatory function of intracellular autonomous replication of a bacterial cell other than actinomycete.

(10) The vector of the above-mentioned (8), wherein the actinomycete belongs to a genus other than the genus *Rhodococcus*.

(11) The vector of the above-mentioned (8), wherein the actinomycete belongs to the genus *Streptomyces*.

(12) The vector of the above-mentioned (9), wherein the bacterial cell other than actinomycete is *Escherichia coli*.

(13) A transformant transformed with the vector of any of the above-mentioned (8) to (12).

(14) A transformant belonging to an actinomycete other than the genus *Rhodococcus*, which has been transformed with a vector functionally comprising both a DNA construct comprising a first promoter that is a nitrilase gene promoter, a structural gene and a nitrilase transcription regulatory protein gene, and a DNA involved in a regulatory function of intracellular autonomous replication of actinomycete.

(15) A transformant belonging to actinomycete, which has been transformed with a vector functionally comprising both a DNA construct comprising a first promoter that is a nitrilase gene promoter, a structural gene, a nitrilase transcription regulatory protein gene and a second promoter placed at the upstream of the nitrilase transcription regulatory protein gene, and a DNA involved in a regulatory function of intracellular autonomous replication of actinomycete.

(16) The transformant of the above-mentioned (15), wherein the second promoter is a nitrilase gene promoter.

(17) The transformant of any of the above-mentioned (14) to (16), wherein the structural gene is a nitrilase gene.

(18) A transformant belonging to an actinomycete other than the genus *Rhodococcus*, into which a DNA construct comprising a first promoter that is a nitrilase gene promoter, a structural gene and a nitrilase transcription regulatory protein gene has been introduced.

(19) A transformant belonging to actinomycete, into which a DNA construct comprising a first promoter that is a nitrilase gene promoter, a structural gene, a nitrilase transcription regulatory protein gene and a second promoter placed at the upstream of the nitrilase transcription regulatory protein gene, has been introduced.

(20) The transformant of the above-mentioned (19), wherein the second promoter is a nitrilase gene promoter.

(21) The transformant of any of the above-mentioned (18) to (20), wherein the structural gene is a nitrilase gene.

(22) A structural gene expression system which comprises expression of a vector functionally comprising both a DNA construct comprising a first promoter that is a nitrilase gene promoter, the structural gene and a nitrilase transcription regulatory protein gene, and a DNA involved in a regulatory function of intracellular autonomous replication of actinomycete, under the control of an inducer in a host belonging to actinomycete other than the genus *Rhodococcus*.

(23) A structural gene expression system which comprises expression of a vector functionally comprising both a DNA construct comprising a first promoter that is a nitrilase gene promoter, the structural gene, a nitrilase transcription regulatory protein gene and a second promoter placed at the upstream of the nitrilase transcription regulatory protein gene, and a DNA involved in a regulatory function of intracellular autonomous replication of actinomycete, under the control of an inducer in an actinomycete host.

(24) The system of the above-mentioned (23), wherein the second promoter is a nitrilase gene promoter.

(25) A structural gene expression system which comprises expression of the structural gene in a host belonging to actinomycete other than the genus *Rhodococcus*, into which a DNA construct comprising a first promoter that is a nitrilase gene promoter, the structural gene and a nitrilase transcription regulatory protein gene has been introduced, under the control of an inducer.

(26) A structural gene expression system which comprises expression of the structural gene in an actinomycete host, into which a DNA construct comprising a first promoter that is a nitrilase gene promoter, the structural gene, a nitrilase transcription regulatory protein gene and a second promoter placed at the upstream of the nitrilase transcription regulatory protein gene, has been introduced, under the control of an inducer.

(27) The system of the above-mentioned (26), wherein the second promoter is a nitrilase gene promoter.

(28) The system of any of the above-mentioned (22) to (27), wherein the structural gene is a nitrilase gene.

(29) A production method of a gene product encoded by a structural gene, which comprises expression of a vector functionally comprising both a DNA construct comprising a first promoter that is a nitrilase gene promoter, the structural gene and a nitrilase transcription regulatory protein gene, and a DNA involved in a regulatory function of intracellular autonomous replication of actinomycete, in an actinomycete other than the genus *Rhodococcus* under the control of an inducer.

(30) A production method of a gene product encoded by a structural gene, which comprises expression of a vector functionally comprising both a DNA construct comprising a first promoter that is a nitrilase gene promoter, the structural gene, a nitrilase transcription regulatory protein gene and a second promoter placed at the upstream of the nitrilase transcription regulatory protein gene, and a DNA involved in a regulatory function of intracellular autonomous replication of actinomycete, in an actinomycete under the control of an inducer.

(31) The production method of the above-mentioned (30), wherein the second promoter is a nitrilase gene promoter.

(32) The production method of any of the above-mentioned (29) to (31), wherein the structural gene is a nitrilase gene.

(33) A production method of a gene product encoded by a structural gene, which comprises expression, under the control of an inducer, of the structural gene in a host belonging to actinomycete other than the genus *Rhodococcus* into which a DNA construct comprising a first promoter that is a nitrilase gene promoter, the structural gene and a nitrilase transcription regulatory protein gene has been introduced.

(34) A production method of a gene product encoded by a structural gene, which comprises expression, under the control of an inducer, of the structural gene in a host belonging to actinomycete into which a DNA construct comprising a first promoter that is a nitrilase gene promoter, the structural gene, a nitrilase transcription regulatory protein gene and a second promoter placed at the upstream of the nitrilase transcription regulatory protein gene has been introduced.

(35) The production method of the above-mentioned (34), wherein the second promoter is a nitrilase gene promoter.

(36) The production method of any of the above-mentioned (33) to (35), wherein the structural gene is a nitrilase gene.

DETAILED DESCRIPTION OF THE INVENTION

Figure 1:
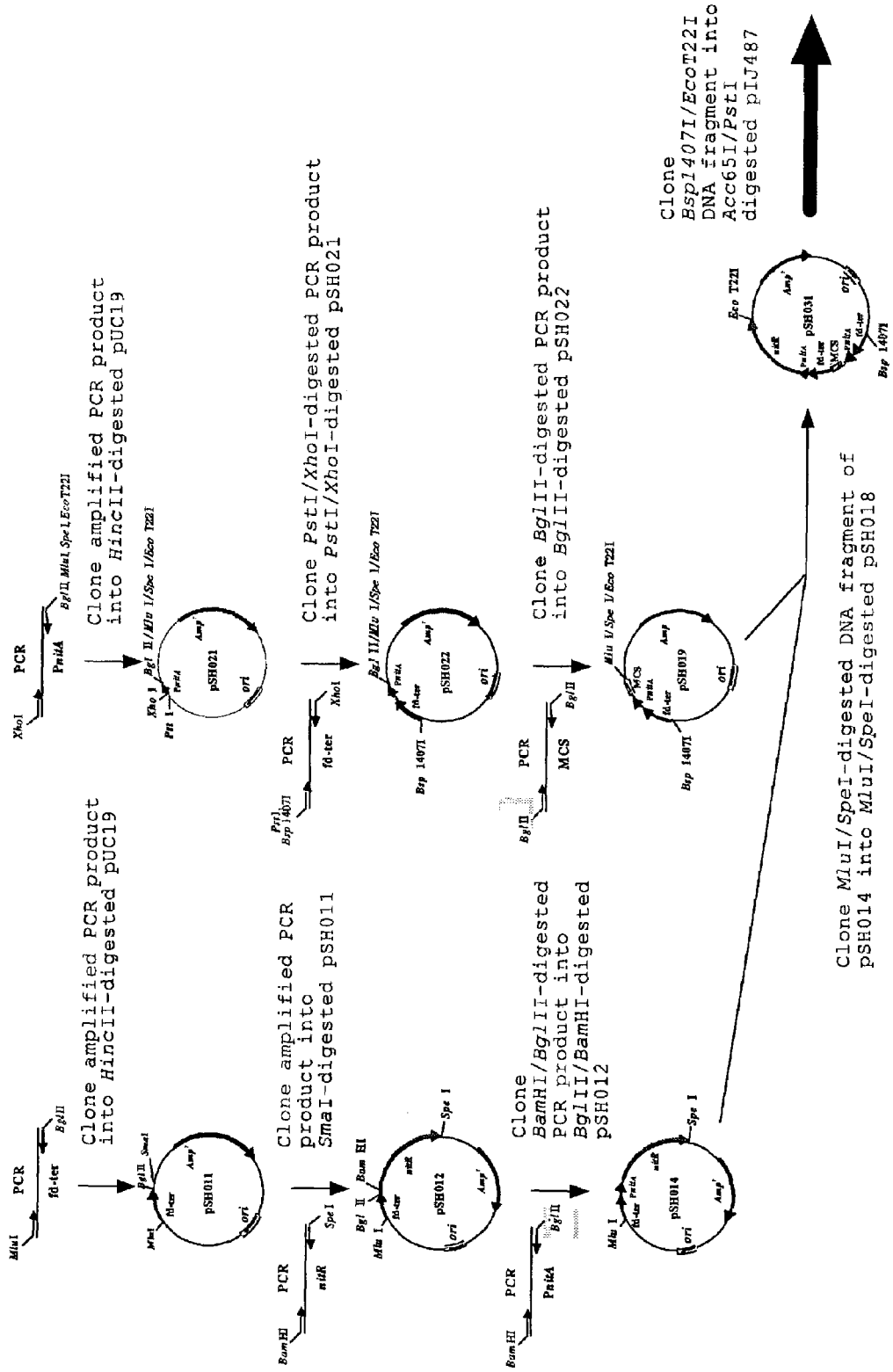
FIG. 1 schematically shows one example of the construction method of the expression vector of the present invention.

The present invention provides a DNA construct comprising a first promoter that is a nitrilase gene promoter, a nitrilase structural gene, a nitrilase transcription regulatory protein gene and a second promoter placed at the upstream of the nitrilase transcription regulatory protein gene. As used herein, by the "DNA construct" is meant the same as a DNA. This term is used for clarifying that it contains respective elements.

The nitrilase gene promoter, the nitrilase gene and the nitrilase transcription regulatory protein gene, which constitute said DNA construct, are already known. For example, The Journal of Biological Chemistry, Oct. 15, 1992, No. 267, pp. 20746-20751 reports a nitrilase gene derived from *Rhodococcus rhodochrous* J1 strain, wherein this gene is obtained as plasmid pNJ10 inserted into vector pUC19. The gene can be prepared by digesting this plasmid with a suitable restriction enzyme. By variously selecting restriction enzymes to be used for the digestion based on the sequence, a gene fragment having at least one, preferably two, more preferably all, of the regions of a nitrilase gene promoter, a nitrilase gene and a nitrilase transcription regulatory protein gene, can be obtained. Conveniently, pNJ10 is digested with a restriction enzyme such as PstI and the like, whereby a gene fragment containing nitrilase gene promoter, nitrilase gene and nitrilase transcription regulatory protein gene can be obtained.

In the present invention, the nitrilase gene promoter is exemplified by a DNA having a base sequence depicted in SEQ ID; No. 15. This DNA may have a base sequence wherein one to several bases have been deleted, substituted, inserted or added, as long as it has a transcription activity of the structural gene (e.g., nitrilase gene) under its control and can be positively controlled by a nitrilase transcription regulatory protein. Alternatively, it may be a DNA fragment containing the base sequence (including a deleted, substituted, inserted or added base sequence).

It may be a DNA capable of hybridizing with a DNA having a base sequence depicted in, for example, SEQ ID; No. 15 under stringent conditions, as long as it has such promoter activity. In the present invention, the stringent conditions means those under which a DNA having a homology of not less than about 60% of the base sequence can hybridize, wherein the stringency can be adjusted by appropriately changing temperature and salt concentration of the hybridizing reaction and washing, and the like. Such promoter can be obtained based on a sequence of nitrilase gene or nitrilase promoter gene and the like by, for example, performing Southern blotting and PCR with the genomic library of a microorganism capable of expressing nitrilase.

When a nitrilase gene promoter, a nitrilase gene and a nitrilase transcription regulatory protein gene are obtained as two or more independent gene fragments, any vector can be used as a base to ligate these gene fragments. A vector suitable for the object thereof and the host to be used is selected. For example, pUC19 having a multicloning site, promoter-probe vector pIJ487 for the genus *Streptomyces*, pPK4 which is a vector for the genus *corynebacterium*, pUB110 for the genus *Bacillus*, pKT263 for the genus *Pseudomonas*, pTT8 for the genus *Thermus* and the like, which are all commercially available or known from a reference.

In the DNA construct of the present invention, the second promoter to be placed at the upstream of the nitrilase transcription regulatory protein gene is not particularly limited as long as it has a promoter activity to transcribe the nitrilase transcription regulatory protein gene in a host. More particularly, a promoter region having a high transcription activity of a nitrilase transcription regulatory protein gene and a part thereof having a promoter activity are exemplified. Specific examples thereof include a nitrilase gene promoter that positively controls the expression of a nitrilase transcription regulatory protein gene in the presence of an inducer (to be mentioned below). It is also possible to use a thiostrepton-inducible promoter and the like as a promoter. A sequence other than these regions (−35 region, −10 region), which are responsible for the promoter activity, can be determined as appropriate for convenient vector construction and the like. In addition, modification of a promoter region is possible. Furthermore, the promoter may be inducible type or constitutive type.

The gene fragment and the above-mentioned vector can be ligated by any known method. For example, a commercially available ligation kit can be used for ligation.

By the "upstream" is meant that the second promoter is in the condition for control of the transcription of the nitrilase transcription regulatory protein gene, and is not limited as regards the position on the DNA construct as long as the second promoter can exhibit its promoter activity.

The present invention also provides a DNA construct containing a first promoter that is a nitrilase gene promoter, a multicloning site and a nitrilase transcription regulatory protein gene.

The nitrilase gene promoter (and a gene fragment including same) and the nitrilase transcription regulatory protein gene (and a gene fragment including same), which constitute the DNA construct, are as mentioned above. The multicloning site can be obtained as a gene fragment having the multicloning site from a known and generally available vector having a multicloning site by cleaving out the corresponding region by digestion with a suitable restriction enzyme or amplification by PCR. The DNA construct of the present invention can be obtained by ligating the gene fragment and the above-mentioned nitrilase gene promoter (and a gene fragment including same) and the nitrilase transcription regulatory protein gene (and a gene fragment including same) according to a known method, such as using a commercially available ligation kit. Conveniently, a nitrilase gene promoter (and a gene fragment including same) and a nitrilase transcription regulatory protein gene (and a gene fragment including same) are inserted into a vector having a multicloning site, using a suitable restriction enzyme. As the vector having a multicloning site, any vector generally used in this field can be used, which is preferably pUC19, pBluescript or pET-21a(+).

A vector containing the DNA construct is useful as a cloning vector because it has a multicloning site.

It is also possible to set a cloning site instead of a multicloning site and to obtain a DNA construct. A vector containing such DNA construct is useful as a cloning vector.

In the DNA construct of the present invention containing a first promoter that is a nitrilase gene promoter, a multicloning site and a nitrilase transcription regulatory protein gene, a second promoter (aforementioned) can be placed at the upstream of the nitrilase transcription regulatory protein gene to control expression thereof. Such embodiment is more preferable for expression in a host of a vector (this vector is obtained by ligating a structural gene into the multicloning site, to be mentioned below), because control of the expression of the structural gene by the first promoter and control of the expression of the nitrilase transcription regulatory protein gene by the second promoter. The second promoter is preferably a nitrilase gene promoter, which up-regulates expression of the nitrilase transcription regulatory protein gene in the presence of an inducer, and increases the expression of a structural gene by potentiating the promoter activity of the nitrilase gene promoter, which is a first promoter.

In the present invention, a desired structural gene can be ligated into the above-mentioned multicloning site. The structural gene is not particularly limited as long as it is a gene encoding various proteins, and exemplified by a gene encoding a desired protein [e.g., enzyme such as nitrilase, cholesterol oxidase and enzymes involved in the biosynthesis of secondary metabolite, peptide having physiological activity such as insulin etc. and the like] and the like, which may be obtained by any method. For example, complementary DNA (cDNA) prepared from mRNA, genomic DNA prepared from genomic library, chemically synthesized DNA, DNA obtained by amplification by PCR using RNA or DNA as a template and DNA constructed by appropriately combining these method and the like can be recited.

Ligation of a structural gene into a multicloning site can be conducted according to a method conventionally employed in the pertinent field, by digestion with various restriction enzymes in combination and ligation of the obtained gene fragments using a commercially available ligation kit and the like.

In the present invention, read through of the transcription from the upstream is prevented by terminator region(s) placed upstream of the first promoter and/or the second promoter, preferably upstream of both the first promoter and the second promoter. The terminator usable in the present invention is free of any particular limitation as long as it matches the host used for the expression of the objective structural gene. Examples thereof include terminator of fd phage (fd-ter), T4 terminator (T4-ter) and the like.

The present invention provides a vector functionally containing both the above-mentioned DNA construct of the present invention, and a DNA of the region involved in a regulatory function of intracellular autonomous replication of actinomycete. As used herein, by "functionally" is meant achievement of a series of phenomena of activation of transcription and expression of the structural gene (particularly nitrilase structural gene) by the first promoter, as well as activation of transcription and expression of the nitrilase transcription regulatory protein gene (when a second promoter is present, this second promoter contributes to the activation of transcription and expression of the transcription regulatory protein gene), and activation of the first promoter by the expressed nitrilase transcription regulatory protein, and that each DNA is autonomously replicatably located in the vector in a host cell. It is possible to contain, in addition to the DNA of the region involved in a regulatory function of intracellular autonomous replication of actinomycete, a DNA of the region involved in a regulatory function of intracellular autonomous replication of bacterial cell other than that of actinomycete, and such vector is useful as a shuttle vector.

The DNA of the region involved in a regulatory function of intracellular autonomous replication of actinomycete is exemplified by those derived from actinomycete vector such as Ori region derived from pIJ, Ori region derived from SCP2, Ori region derived from pPK4, which is autonomously replicatable in the genus *Corynebacterium*, Ori region derived from pCG1 and the like.

The DNA of the region involved in a regulatory function of intracellular autonomous replication of a bacterial cell other than actinomycete is appropriately determined depending on a host whose autonomous replication is desired. Examples thereof include Ori region derived from pUC, Ori region derived from p15A, Ori region derived from pSC101 and the like, which are capable of autonomous replication in *Escherichia coli*, Ori region derived from pUB110, which is capable of autonomous replication in the bacteria belonging to the genus *Bacillus* (this Ori is originally derived from the genus *Staphylococcus*), Ori region derived from pKT263, which is capable of autonomous replication in the bacteria belonging to the genus *Pseudomonas*, Ori region derived from pTT8, which is capable of autonomous replication in the bacteria belonging to the genus *Thermus* and the like.

The "actinomycete" in the present invention is defined as the order Actinomycetales in the class Actinobacteria created based on the analogy of 16S rDNA by Stackebrandt et al. in 1997, and includes 10 suborders, 35 families, about 110 genera, and about 1000 species (e.g., The Society for Actinomycetes Japan ed., Identification Manual of Actinomycetes, Foundation Business Center for Academic Societies Japan, February 2001, pp. 4-8).

The transformant in the present invention is prepared by introducing a vector (including shuttle vector, recombinant vector, cloning vector and the like) obtained above into a suitable host cell. The host cell is determined depending on the vector, and for example, a vector having a DNA involved in a regulatory function of intracellular autonomous replication in actinomycete can use actinomycete as a host, and a shuttle vector having a DNA involved in a regulatory function of intracellular autonomous replication in *Escherichia coli* can use *Escherichia coli* as a host.

Examples of the host other than actinomycete include *Escherichia coli*, a strain belonging to the genus *Bacillus*, a strain belonging to the genus *Pseudomonas*, a strain belonging to the genus *Thermus*, a strain belonging to the genus *Agrobacterium* and the like.

The preparation method of transformant is not particularly limited and can be appropriately determined depending on the host, and can be prepared using a conventionally known method or an appropriately modified method. To be specific, competent cell method, protoplast-polyethylene glycol fusion method, calcium phosphate coprecipitation method, DEAE dextran method, microinjection method, electroporation method and the like can be exemplified.

In the present invention, for confirmation if the host has been transformed accurately, a selection marker gene (e.g., antibiotic resistance gene such as kanamycin resistance gene, thiostrepton resistance gene, ampicillin resistance gene and the like, enzyme gene such as auxotrophy gene, lacZ and the like, and the like) may be introduced into a vector. As regards those permitting confirmation of the transformation with an expression vector by way of an expression of a structural gene, such as enzyme activity and the like, the confirmation is made based on the expression.

When desired, a replication factor region can be contained and, for example, rep derived from pIJ can be used.

In the present invention, the OriT region (origin of transfer) can be contained in the vector. The vector having such region can be introduced into actinomycete by conjugal transfer.

It is possible to obtain a transformant having desired properties by directly substituting the DNA construct of the present invention with a promoter region on the chromosome by homologous recombination and the like, without using the DNA construct as a vector for transmission.

Accordingly, the transformant of the present invention encompasses a host cell into which the above-mentioned DNA construct has been introduced by conjugation and homologous recombination, which can be prepared according to the method generally practiced in this field. When a transformant is prepared by homologous recombination and the like, the DNA construct to be introduced does not particularly need to have in itself a DNA involved in a regulatory function of autonomous replication in the host.

The obtained transformant can be cultured in an appropriate culture medium generally used in this field depending on the cell species thereof. For example, a medium containing polypeptone, yeast extract, malt extract and the like is used for actinomycete. The culture time and culture temperature are also appropriately determined depending on the cell species thereof. When the expression of structural gene, such as nitrilase structural gene, is done by an inducer, a given inducer is used to induce its expression, whereby nitrilase can be obtained. A method for harvesting a useful protein and the like encoded by a structural gene, from a bacterial cell, a bacterial cell suspension and the like is similar to the method generally employed in this field and appropriately selected depending on the host. For example, when *Escherichia coli* is used as a host, the produced protein may be present as an inclusion body without going out from the cell, and cell lysis using a surfactant and the like becomes necessary. When actinomycete is used as a host, it needs to be secreted extracellularly and be harvested from a culture supernatant. For confirmation of the production of nitrilase, for example, the following method can be employed. A transformant is cultured to give a bacterial cell suspension, to which benzonitrile as a substrate is added. When nitrilase gene is expressed, benzonitrile is converted to benzoic acid by the action of the produced nitrilase. Accordingly, the expression of nitrilase gene can be confirmed depending on the presence or otherwise of the production thereof.

The present invention provides a method for expression of a nitrilase structural gene (hereinafter this method is referred to as a nitrilase structural gene expression system), as well as a production method of a gene product encoded by the structural gene. This system and this method are characterized by the expression of a vector functionally containing both a DNA construct comprising a first promoter that is a nitrilase gene promoter, a structural gene and a nitrilase transcription regulatory protein gene, and a DNA involved in a regulatory function of intracellular autonomous replication of actinomycete, in an actinomycete host other than the genus *Rhodococcus* under the control of an inducer. The details of respective elements and steps constituting this expression system and the production method are as mentioned above.

When the structural gene is nitrilase gene, the DNA construct of the present invention can be obtained along with a nitrilase gene promoter and a nitrilase transcription regulatory protein gene from, for example, pNJ10. When a structural gene other than nitrilase gene is contained, a multicloning site can be used (needless to say that even a nitrilase gene can be inserted using a multicloning site). The method for confirming the expression of the structural gene is appropriately determined depending on the properties of the desired protein encoded by the structural gene. In the case of a gene encoding an enzyme, its expression can be confirmed by measuring the enzyme activity.

The "actinomycete host other than genus *Rhodococcus*" is actinomycete that does not belong to the genus *Rhodococcus*, from among the "actinomycete" including about 110 genera, as mentioned above. Examples thereof include strains belonging to the genus *Streptomyces*, the genus *Corynebacterium*, and the genus *Nocardiaceae*. The "inducer" is not particularly limited as long as it can induce a nitrilase gene promoter, which is a first promoter. Examples thereof include ε-caprolactam, isobutyronitrile and the like, which are all commercially available.

Preferably, a second promoter (preferably nitrilase gene promoter) is placed at the upstream (aforementioned) of a nitrilase transcription regulatory protein gene.

The present invention provides a method for expression of a structural gene (hereinafter this method is referred to as a structural gene expression system), as well as a production method of a gene product encoded by the structural gene. This system and this method are characterized by the expression, under the control of an inducer, of a vector functionally containing both a DNA construct comprising a first promoter that is a nitrilase gene promoter, a structural gene and a nitrilase transcription regulatory protein gene (the construct also has a second promoter (preferably nitrilase gene promoter) placed at the upstream of the nitrilase transcription regulatory protein gene), and a DNA involved in a regulatory function of intracellular autonomous replication of actinomycete, in an actinomycete host. The details of respective elements and steps constituting this expression system and the production method are as mentioned above.

As regards the "inducer", when a nitrilase gene promoter is used as a second promoter, an inducer such as those exemplified for the first promoter can be used, or the same inducer used for the first promoter can be used for the second promoter as well. When the second promoter is not the nitrilase gene promoter but a different inducible promoter, an inducer suitable for the promoter is used. For example, when a thiostrepton inducible promoter is used, thiostrepton is used as the inducer.

In these expression system and production method, a method for confirmation of the expression of the structural gene can be appropriately determined depending on the properties of the desired protein encoded by the structural gene. When the gene encodes an enzyme, the expression can be confirmed by measuring the enzyme activity. For example, the expression of a nitrilase gene can be confirmed using conversion of benzonitrile to benzoic acid as an index, as mentioned above.

Moreover, the present invention provides another method for expression of a structural gene (hereinafter this method is also referred to as a structural gene expression system), as well as a production method of a gene product encoded by the structural gene. This system and this method are characterized by the expression of the structural gene in an actinomycete host other than the genus *Rhodococcus*, into which a DNA construct comprising a first promoter that is a nitrilase gene promoter, a structural gene and a nitrilase transcription regulatory protein gene, has been introduced, under the control of an inducer. The details of respective elements and steps constituting this expression system and the production method, and a method for confirmation of the expression are as mentioned above.

Furthermore, the present invention provides a method for expression of a structural gene (hereinafter this method is also referred to as a structural gene expression system), as well as a production method of a gene product encoded by the structural gene. This system and this method are characterized by the expression of the structural gene in an actinomycete host, into which a DNA construct comprising a first promoter that is a nitrilase gene promoter, a structural gene and a nitrilase transcription regulatory protein gene (the construct also has a second promoter placed at the upstream of the nitrilase transcription regulatory protein gene) has been introduced, under the control of an inducer. The details of respective elements and steps constituting this expression system and the production method, and a method for confirmation of the expression are as mentioned above.

One embodiment of the vector of the present invention and an expression system using the same is explained in the following (FIG. 1).

(1) Construction of pSH011

Using (fd-ter retained by) pIJ487 as a template, MluI site-added primer (5'-CGACGCGTTCCCCGCAAAAGCGGC-CTTT-3' [28mer]: SEQ ID; No. 1) and BglII site-added primer (5'-GAAGATCTTCTAAAGTTTTGTCGTCTTT-3' [28mer]: SEQ ID; No. 2) are applied to PCR and an amplified fragment is inserted into HincII site of pUC19 in the same direction with ampicillin resistance gene (Amp$^r$), whereby pSH011 is constructed.

(2) Construction of pSH012

Separately, using (nitR retained by) pNJ487 as a template, BamHI site-added primer (5'-CGGGATCCACGGCTAC- CCTGAAAAGAGC-3' [28mer]: SEQ ID; No. 3) and SpeI site-added primer (5'-GGACTAGTCCGGGCTCTTCCTAC-GAAAC-3' [28mer]: SEQ ID; No. 4) are applied to PCR and an amplified fragment is inserted into the SmaI site of pSH011 obtained in the above-mentioned (1) in the same direction with ampicillin resistance gene, whereby pSH012 is constructed.

(3) Construction of pSH014

Separately, using (nitA promoter retained by) pNJ10 as a template, BamHI site-added primer (5'-CGGGATCCGC-GAACTCCCTTATGCGGGT -3' [28mer]: SEQ ID; No. 5) and BglII site-added primer (5'-GAAGATCTGTTGCTTGT-GTTTGGCAGGA-3' [28mer]: SEQ ID; No. 6) are applied to PCR, and the amplified fragment is digested with BamHI and BglII and inserted into the pSH012 (obtained in the above-mentioned (2)) digested with BamHI and BglII in the same direction with fd-ter and nitR, whereby pSH014 is constructed. Insertion in this direction gives binding sites of BamHI/BglII for both.

(4) Construction of pSH021

Separately, using (nitA promoter retained by) pNJ10 as a template, XhoI site-added primer (5'-CGCTCGAGGC-GAACTCCCTTATGCGGGT -3' [28mer]: SEQ ID; No. 7) and EcoT22I/SpeI/MluI/BglII site-added primer (5'-CGAT-GCATACTAGTACGCGTAGATCTGTTGCT-TGTGTTTGGCAGGACAGTACGAGG -3' [56mer]: SEQ ID; No. 8) are applied to PCR and the amplified fragment is inserted into the HincII site of pUC19 in the same direction with ampicillin resistance gene, whereby pSH021 is constructed.

(5) Construction of pSH022

Using (fd-ter retained by) pIJ487 as a template, PstI/Bsp1407I site-added primer (5'-AACTGCAGTGTACATC-CCCGCAAAAGCGGCCTTT -3' [34mer]: SEQ ID; No. 9) and XhoI site-added primer (5'-CCGCTC-GAGTCTAAAGTTTTGTCGTCTTT-3' [29mer]: SEQ ID; No. 10) are applied to PCR, and the amplified fragment is digested with PstI and XhoI and inserted into the pSH021 (obtained in the above-mentioned (4)) digested with PstI and XhoI in the same direction with fd-ter, whereby pSH022 is constructed.

(6) Construction of pSH019

Using pUC19 as a template, BglII site-added primer (5'-CAACAAGATCTGAATTCGAGCTCGGTACC -3' [29mer]: SEQ ID; No. 11) and BglII site-added primer (5'-CGAGAAGATCTAAGCTTGCATGCCTGCAG-3' [29mer]: SEQ ID; No. 12) are applied to PCR, and the amplified fragment is digested with BglII and inserted into the pSH022 (obtained in the above-mentioned (5)) digested with BglII in the direction that makes HindIII site upstream of EcoRI site, relative to the transcription direction of nitA promoter of pSH022, whereby pSH019 is constructed.

(7) Construction of pSH031

The pSH014 obtained in the above-mentioned (3) is digested with MluI and SpeI to give a small fragment (=fragment containing fd-ter, nitA promoter and nitR), which is inserted into the pSH019 (obtained in the above-mentioned (6)) digested with MluI and SpeI, whereby pSH031is constructed.

(8) Construction of pSH19

Figure 2:
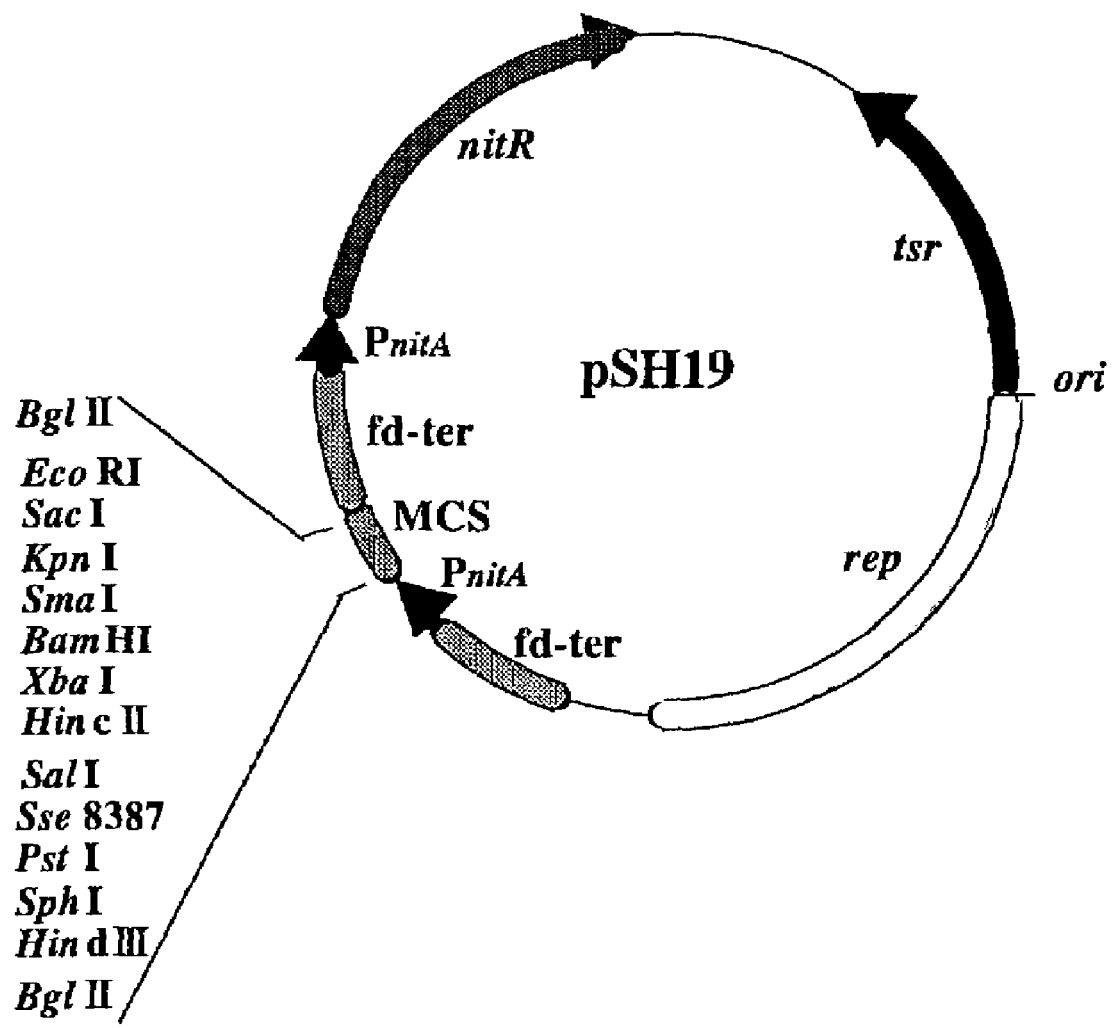
FIG. 2 shows the novel inducible high expression vector of the present invention.

The pSH031 obtained in the above-mentioned (7) is digested with Bsp1407I and EcoT22I and ligated with a fragment containing fd-ter, nitA promoter, multicloning site (hereinafter also simply MCS), fd-ter, nitA promoter and nitR, and a fragment containing a plasmid replication site in actinomycete and a thiostrepton resistance gene obtained by digesting pIJ487 with Acc65I and PstI, thereby to give the vector of the present invention, pSH19 (FIG. 2).

As a result, the obtained pSH19 has a thiostrepton resistance gene frequently used as a selection marker for the genus Streptomyces, can use all restriction enzymes producing cohesive end, which are present in BglII site as well as in multicloning site of pUC19, and advantageously permits easy construction of expression vector.

EXAMPLES

The present invention is explained in detail in the following by referring to Examples, which are not to be construed as limitative.

In the following Examples, unless otherwise particularly specified, materials and reagents generally used for preparation of. recombinant vector (e.g., digestion reaction by restriction enzymes, ligation reaction, confirmation of such reactions and the like) are commercially available, and the conditions of each reaction (reaction temperature, reaction pH, salt concentration of buffer, reaction time and the like) can be appropriately determined depending on the enzymes to be used and the like and follow recommendations of the manufacturer thereof.

Example 1

Figure 3:
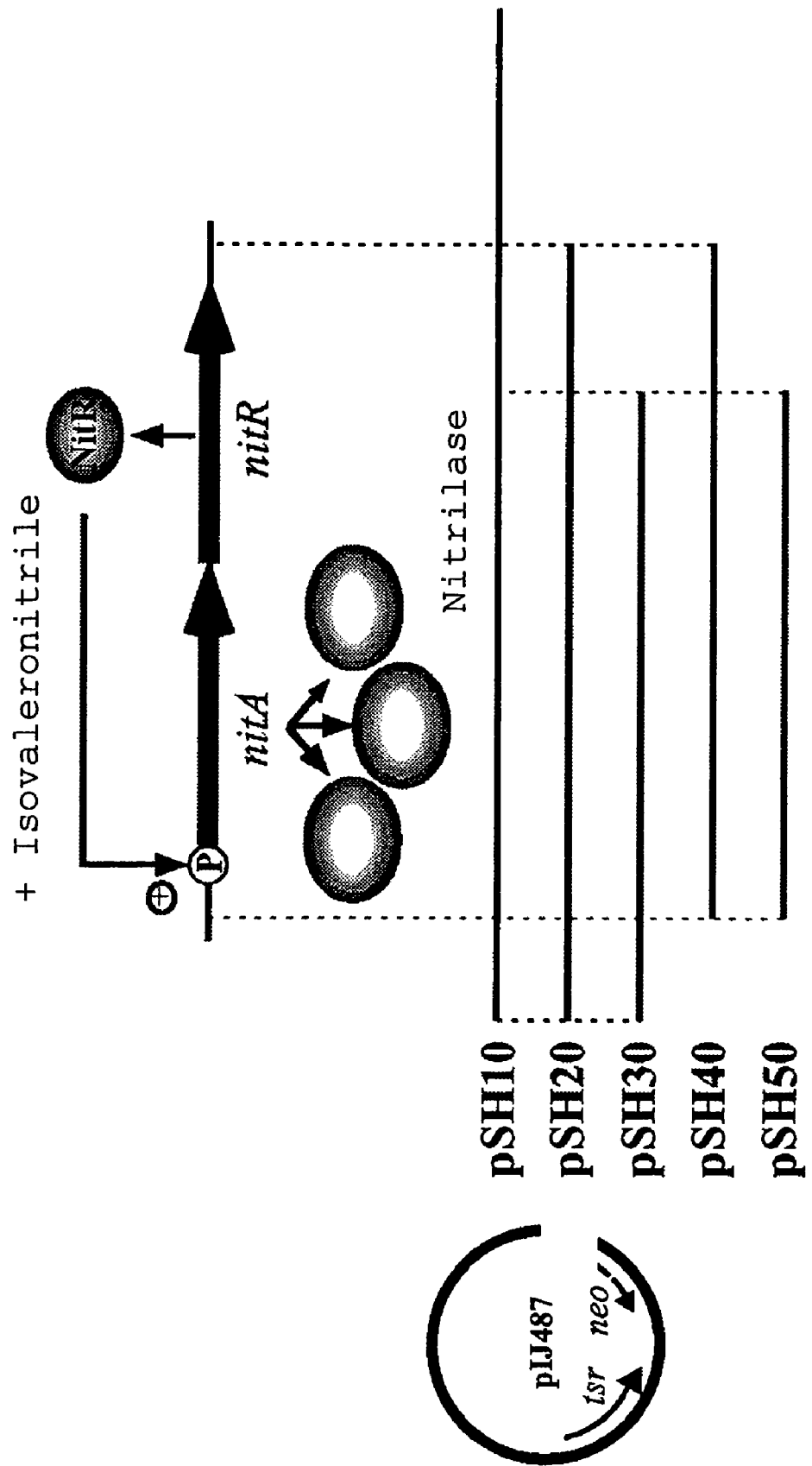
FIG. 3 shows the constitution of various plasmid vectors comprising a nitA promoter, a nitA gene and a nitR gene, with deletion of a part of an expression unit.

Examination of Inducible Expression System of Nitrilase (1) Preparation of Plasmid Containing Nitrilase Gene and Nitrilase Transcription Regulatory Protein Gene (see FIG. 3)

The gene fragment was cleaved out from a plasmid containing a nitrilase gene fragment of *Rhodococcus rhodochrous* J1 strain, and inserted into PstI site of promoter probe vector pIJ487 for actinomycete to give a recombinant plasmid. In addition, a plasmid containing a region shorter than the aforementioned PstI fragment was prepared by insertion.

First, a 5.4 kb PstI fragment containing nitrilase gene of *Rhodococcus rhodochrous* J1 strain was inserted into a vector to obtain plasmid pNJ10 (see Proceedings of the National Academy of Sciences USA, October 1996, No. 93, pp. 10572-10577), from which a 5.4 kb PstI fragment was cleaved out and ligated with pBluescript SK+ digested with PstI, whereby a plasmid pSK+10 was constructed, in which the 5.4 kb PstI fragment had been inserted in the direction such that NheI site of PstI fragment was near XbaI site of the pBluescript SK+ (see JP-A-9-28380 for detail of the restriction enzyme site in the 5.4 kb PstI fragment).

A 3.6 kb PstI-EcoT22I fragment was cleaved out from pNJ10 and ligated with pBluescript SK+ digested with PstI, whereby a plasmid pSK+20 was constructed, in which the 3.6 kb PstI-EcoT22I fragment had been inserted in the direction such that NheI site of PstI-EcoT22I fragment was near XbaI site of the pbluescript SK+.

A 2.8 kb PstI-NaeI fragment was cleaved out from pNJ10 and ligated with pBluescript SK+ digested with PstI-HincII, whereby pSK+30 was constructed.

pSH10 was constructed by cleaving out a XbaI-HindIII fragment (including nitA promoter, nitA and nitR) from pSK+10 and ligating the fragment with a promoter probe vector pIJ487 for actinomycete digested with the same restriction enzyme (Genetic manipulation of *Streptomyces*: a laboratory manual. (Hopwood, D. A-., M. J. Bibb, K. F. Chater, T. Kieser, C. J. Bruton, H. M. Kieser, D. J. Lydiate, C.

P. Smith, J. M. Ward, and H. Schrempf. 1985. The John Innes Foundation, Norwich, United Kingdom)).

pSH20 was constructed by cleaving out a XbaI-HindIII fragment (containing nitA promoter, nitA and nitR) from pSK+20 and ligating the fragment with pIJ487 digested with the same restriction enzyme.

pSH30 was constructed by cleaving out a XbaI-HindIII fragment (containing nitA promoter and nitA) from pSK+30 and ligating the fragment with pIJ487 digested with the same restriction enzyme. The pSH30 lacked the C-terminal side of the transcription regulatory protein NitR.

pSH40 contained a nitrilase gene and all the regulatory proteins thereof and lacked the upstream region of the NheI site upstream of the nitrilase gene. pSH40 was constructed by cleaving out an NheI-HindIII fragment (containing nitA promoter, nitA and nitR) from pSK+20 and ligating the fragment with pIJ487 digested with XbaI-HindIII.

pSH50 was constructed by cleaving out an NheI-HindIII fragment (containing nitA promoter, nitA) from pSK+30 and ligating the fragment with pIJ487 digested with XbaI-HindIII.

(2) Preparation of Transformant Belonging to the Genus *Streptomyces* and Assay of Nitrilase Activity Each plasmid obtained in the above-mentioned (1) was introduced into *Streptomyces lividans* (*S. lividans*) TK24 strain (genetic manipulation of *Streptomyces*: a laboratory manual, 1985, the aforementioned), which is one of the bacteria belonging to the genus *Streptomyces*. The transformation followed the method (protoplast-polyethylene glycol fusion method) described in Genetic manipulation of *Streptomyces*: a laboratory manual (the aforementioned). The cells were inoculated to a YEME medium (yeast extract 0.3%, bactopeptone 0.5%, malt extract 0.3%, glucose 1%, sucrose 34%, $MgCl_2$ 5 mM, glycine 0.5%) and shake-cultured at 28° C. After 96 hr, 0.1% ε-caprolactam was added as an inducer (non-addition of the inducer as a comparison control), and the cells were subjected to shake culture for additional 24 hr.

Figures 4A, 4B:
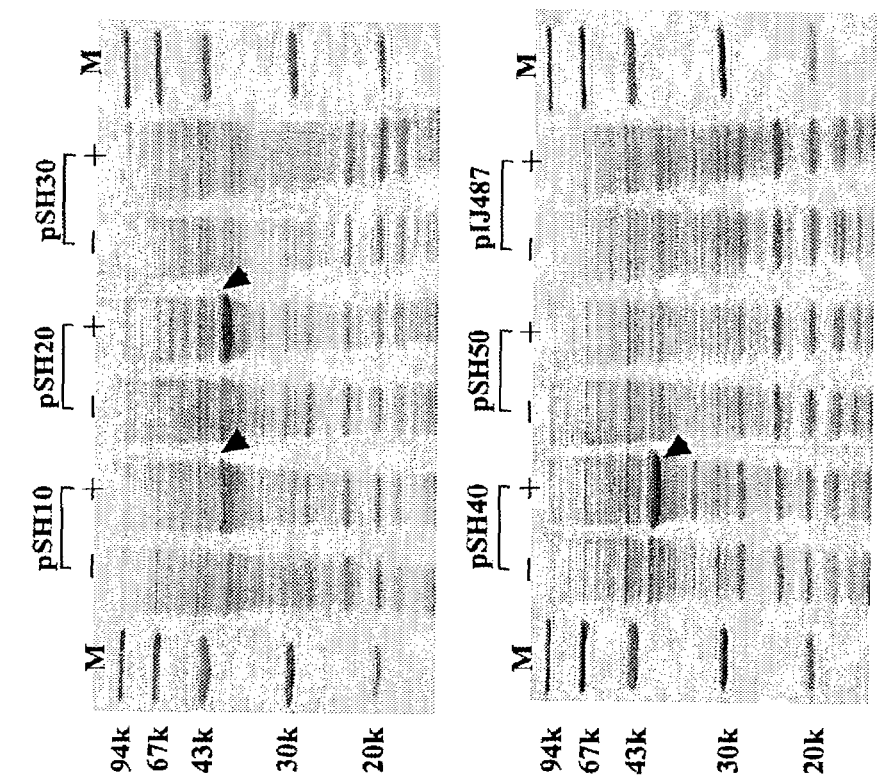
FIG. 4A shows the results of SDS-PAGE analysis of nitrilase proteins produced by the genus *Streptomyces* strain transformed with pSH10, pSH20, pSH30, pSH40 or pSH50
FIG. 4B is a Table showing the results of the activity of nitrilase proteins produced by the genus *Streptomyces* strain transformed with pSH10, pSH20, pSH30, pSH40 or pSH50.

The cells collected by centrifugation separation from the culture broth were washed with 10 mM potassium phosphate buffer (pH 7.5) and suspended in 0.1 M potassium phosphate buffer (pH 7.5) containing 1 mM dithiothreitol. The cells were disrupted by ultrasonication and, using the supernatant (cell-free extract) obtained by centrifugal separation, SDS-PAGE was performed to confirm expression of nitrilase. The nitrilase activity was assayed as follows. To a cell-free extract (0.25 mL) appropriately diluted with water were respectively added 0.25 mL of 0.1 mM potassium phosphate buffer (pH 7.0) and 0.5 mL of 12 mM benzonitrile and, after reaction at 20° C. for 10 min, 1N HCl (0.1 mL) was added to stop the reaction. Benzoic acid produced by the enzyme reaction was analyzed by HPLC. The results of SDS-PAGE and assay of nitrilase activity are shown in FIG. 4.

(3) Results

It is clear that inducible and remarkable nitrilase expression of pSH10, pSH20 and pSH40 occurred in both SDS-PAGE (41.5 kD) and enzyme activity assay. Therefrom it is clear that the protein of actinomycete belonging to the genus *Rhodococcus* expresses in the transcription and translation systems of actinomycete belonging to the genus *Streptomyces*, and that the expression control system derived from *Rhodococcus* functions in *Streptomyces*. Because expression of nitrilase was scarcely confirmed in pSH30 and pSH50 lacking the C-terminal side of NitR, it is clear that the presence of the transcription regulatory protein NitR is essential for the function of the expression control system in the genus *Streptomyces*. When the inducer was added, not only nitA present immediately downstream of the nitA promoter but also nitR present further downstream thereof showed expression as a protein. Therefrom it is considered that this expression system is a potent inducible expression system that can cause expression of even a gene located quite far from the promoter.

From the foregoing results, it has been confirmed that the function of this expression system essentially requires nitA and nitR regions contained in pSH40. In addition, an actinomycete: *Streptomyces griseus* (*S. griseus*) NRRL B-2682 strain (Journal of Bacteriology, 155: 357-366 (1983)) was transformed with pSH40 to give a transformant, which was inoculated to a YEME medium and shake-cultured at 28° C. After 72 hr, 0.1% ε-caprolactam was added as an inducer (non-addition of the inducer as a comparison control), and the cells were subjected to shake culture for additional 24 hr. Similarly as in *Streptomyces lividans* TK24 strain, inducible expression of nitrilase was confirmed by both SDS-PAGE (41.5 kD) and enzyme activity assay.

In addition, an influence of the concentration of the inducer on the expression amount of the nitrilase expression system of the genus *Streptomyces* was examined. As a result, the tendency of increasing nitrilase expression amount was confirmed along with increasing concentrations of the inducer. This tendency of inducer concentration-dependent expression amount is extremely advantageous for the development of a controllable expression system.

Example 2

Development of Novel Inducible Expression System (1) Construction of pSH011

First, using (fd-ter retained by) pIJ487 as a template, MluI site-added primer (5'-CGACGCGTTCCCCGCAAAAGCG-GCCTTT-3' [28mer]: SEQ ID; No. 1) and BglII site-added primer (5'-GAAGATCTTCTAAAGTTTTGTCGTCTTT-3' [28mer]: SEQ ID; No. 2) were applied to PCR and an amplified fragment was inserted into HincII site of pUC19 (TAKARA SHUZO CO., LTD.) in the same direction with ampicillin resistance gene ($Amp^r$), whereby pSH011 was constructed.

PCR conditions:
25 cycles of 94° C. (30 sec)→53° C. (30 sec)→68° C. (60 sec)

(2) Construction of pSH012

Separately, using (nitR retained by) pNJ10 as a template, BamHI site-added primer (5'-CGGGATCCACGGCTAC-CCTGAAAAGAGC-3' [28mer]: SEQ ID; No. 3) and SpeI site-added primer (5'-GGACTAGTCCGGGCTCTTCCTAC-GAAAC -3' [28mer]: SEQ ID; No. 4) were applied to PCR and an amplified fragment was inserted into SmaI site of pSH011 obtained in the above-mentioned (1) in the same direction with ampicillin resistance gene, whereby pSH012 was constructed.

PCR conditions:
25 cycles of 94° C. (30 sec)→53° C. (30 sec)→68° C. (60 sec)

(3) Construction of pSH014

Separately, using (nitA promoter retained by) pNJ10 as a template, BamHI site-added primer (5'-CGGGATCCGC-GAACTCCCTTATGCGGGT -3' [28mer]: SEQ ID; No. 5) and BglII site-added primer (5'-GAAGATCTGTTGCTTGT-GTTTGGCAGGA-3' [28mer]: SEQ ID; No. 6) were applied to PCR, and the amplified fragment was digested with BamHI and BglII and inserted into the pSH012 (obtained in the above-mentioned (2)) digested with BamHI and BglII, in the same direction with fd-ter and nitR, whereby pSH014 was constructed. Insertion in this direction gives binding sites of BamHI/BglII for both.

PCR conditions:
25 cycles of 94° C. (30 sec)→53° C. (30 sec)→68° C. (60 sec)

(4) Construction of pSH021

Separately, using (nitA promoter retained by) pNJ10 as a template, XhoI site-added primer (5'-CGCTCGAGGC-GAACTCCCTTATGCGGGT -3' [28mer]: SEQ ID; No. 7) and EcoT22I/SpeI/MluI/BglII site-added primer (5'-CGAT-GCATACTAGTACGCGTAGATCTGTTGCT-TGTGTTTGGCAGGACAGTACGAGG -3' [56mer]: SEQ ID; No. 8) were applied to PCR and an amplified fragment was inserted into HincII site of pUC19 in the same direction with ampicillin resistance gene, whereby pSH021 was constructed.

PCR conditions:
25 cycles of 94° C. (30 sec)→53° C. (30 sec)→68° C. (60 sec)

(5) Construction of pSH022

Using (fd-ter retained by) pIJ487 as a template, PstI/Bsp1407I site-added primer (5'-AACTGCAGTGTACATC-CCCGCAAAAGCGGCCTTT -3' [34mer]: SEQ ID; No. 9) and XhoI site-added primer (5'-CCGCTC-GAGTCTAAAGTTTTGTCGTCTTT-3' [29mer]: SEQ ID; No. 10) were applied to PCR, and the amplified fragment was digested with PstI and XhoI and inserted into the pSH021 (obtained in the above-mentioned (4)) digested with PstI and XhoI, in the same direction with fd-ter, whereby pSH022 was constructed.

PCR conditions:
25 cycles of 94° C. (30 sec)→53° C. (30 sec)→68° C. (60 sec)

(6) Construction of pSH019

Using pUC19 as a template, BglII site-added primer (5'-CAACAAGATCTGAATTCGAGCTCGGTACC -3' [29mer]: SEQ ID; No. 11) and BglII site-added primer (5'-CGAGAAGATCTAAGCTTGCATGCCTGCAG-3' [29mer]: SEQ ID; No. 12) were applied to PCR, and the amplified fragment was digested with BglII and inserted into the pSH022 (obtained in the above-mentioned (5)) digested with BglII, in the direction that made HindIII site upstream of EcoRI site, relative to the transcription direction of nitA promoter of pSH022, whereby pSH019 was constructed.

PCR conditions:
25 cycles of 94° C. (30 sec)→53° C. (30 sec)→68° C. (60 sec)

(7) Construction of pSH031

The pSH014 obtained in the above-mentioned (3) was digested with MluI and SpeI to give a small fragment (=fragment containing fd-ter, nitA promoter and nitR), which was inserted into the pSH019 (obtained in the above-mentioned (6)) digested with MluI and SpeI, whereby pSH031 was constructed.

(8) Construction of pSH19

Figure 5:
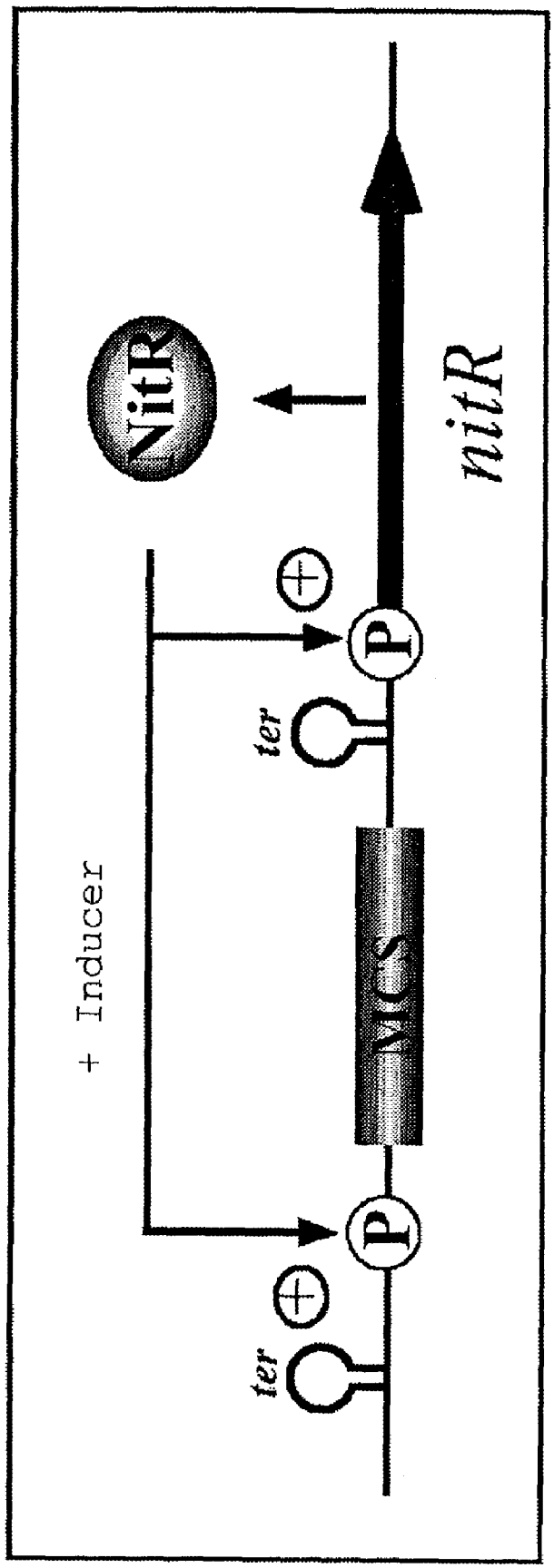
FIG. 5 shows a model of the novel inducible expression system of the present invention.

The pSH031 obtained in the above-mentioned (7) was digested with Bsp1407I and EcoT22I and ligated with a fragment containing fd-ter, nitA promoter, multicloning site (MCS), fd-ter, nitA promoter and nitR, and a fragment containing a plasmid replication site in actinomycete and a thiostrepton resistance gene, which fragment was obtained by digesting pIJ487 with Acc65I and PstI to give the vector of the present invention, pSH19 (FIG. 2). A model pSH19 expression system is shown in FIG. 5.

(9) Confirmation of pSH19 Function

To examine if the constructed expression vector pSH19 actually functions, using a nitrilase gene (nitA) as a template, primer (5'-GCCAAAGCTTAGCAACGGAGGTACGG-3' [26mer]: SEQ ID; No. 13), to which HindIII site and SD sequence for actinomycete had been added, and PstI site-added primer (5'-CGCTGCAGTCAGATGGAGGCTGTCG-3' [25mer]: SEQ ID; No. 14) were applied to PCR, and the amplified fragment is digested with HindIII and PstI and ligated into HindIII site and PstI site in MCS of pSH19, whereby an expression vector (pSH19-SDnitA) with a nitrilase gene as a reporter gene was constructed. The nitrilase expression in a transformant obtained by introducing the vector into an actinomycete: *Streptomyces lividans* TK24 strain was confirmed by the addition or non-addition of an inducer ε-caprolactam to a YEME medium. As a result, nitrilase expressed by the addition of the inducer, and a band showing an excess expression was confirmed in SDS-PAGE. Therefore, it was clarified that the vector pSH19 of the present invention can sufficiently function as an inducible high expression vector.

SEQ ID; No. 1: Oligonucleotide designed to act as PCR primer to amplify the fd-ter region.
SEQ ID; No. 2: Oligonucleotide designed to act as PCR primer to amplify the fd-ter region.
SEQ ID; No. 3: Oligonucleotide designed to act as PCR primer to amplify the nitR region.
SEQ ID; No. 4: Oligonucleotide designed to act as PCR primer to amplify the nitR region.
SEQ ID; No. 5: Oligonucleotide designed to act as PCR primer to amplify the nitA promoter region.
SEQ ID; No. 6: Oligonucleotide designed to act as PCR primer to amplify the nitA promoter region.
SEQ ID; No. 7: Oligonucleotide designed to act as PCR primer to amplify the nitA promoter region.
SEQ ID; No. 8: Oligonucleotide designed to act as PCR primer to amplify the nitA promoter region.
SEQ ID; No. 9: Oligonucleotide designed to act as PCR primer to amplify the fd-ter region.
SEQ ID; No. 10: Oligonucleotide designed to act as PCR primer to amplify the fd-ter region.
SEQ ID; No. 11: Oligonucleotide designed to act as PCR primer.
SEQ ID; No. 12: Oligonucleotide designed to act as PCR primer.
SEQ ID; No. 13: Oligonucleotide designed to act as PCR primer to amplify the nitA region.
SEQ ID; No. 14: Oligonucleotide designed to act as PCR primer to amplify the nitA region.
SEQ ID; No. 15: Oligonucleotide derived from *Rhodococcus rhodochrous*

As a result of the clarification that an inducible high expression system derived from the genus *Rhodococcus* functions in actinomycetes of other genera such as the genus *Streptomyces* and the like, the application of the expression system to various microorganisms industrially used widely as a production bacteria of various useful substances has been made possible. In addition, the development of an expression system, into which a multicloning site has been introduced, and an expression system under control of two promoters affords a large-scale expression system of useful proteins other than nitrilase, and is extremely useful for each field that essentially requires production of antibiotic substances and physiologically active substances, production of useful enzymes and the like.

This application is based on application No. 260679/2002 filed in Japan, the contents of which are incorporated hereinto by reference.

What is claimed is:

1. A DNA construct comprising a first promoter that is a nitrilase gene promoter consisting of the sequence of SEQ ID NO: 15, operably linked to a nitrilase gene from *Rhodococcus rhodochrous* J 1 and a second promoter that is a nitrilase gene promoter consisting of the sequence of SEQ ID NO: 15, wherein the second promoter is placed upstream of a nitrilase transcription regulatory protein gene from *Rhodococcus rhodochrous* J 1.

2. A DNA construct comprising a first promoter that is a nitrilase gene promoter consisting of the sequence of SEQ ID NO: 15, operably linked to a cloning or multi-cloning site and a second promoter that is a nitrilase gene promoter consisting of the sequence of SEQ ID NO: 15, wherein the second promoter is placed upstream of a nitrilase transcription regulatory protein gene from *Rhodococcus rhodochrous* J 1.

3. The DNA construct of claim 1, further comprising a terminator region upstream of the first promoter and/or the second promoter.

4. A vector comprising both the DNA construct of claim 1, and a DNA involved in a regulatory function of intracellular autonomous replication of actinomycete.

5. The vector of claim 4, further comprising a DNA involved in a regulatory function of intracellular autonomous replication of a bacterial cell other than actinomycete.

6. The vector of claim 4, wherein the actinomycete belongs to a genus other than the genus *Rhodococcus*.

7. The vector of claim 4, wherein the actinomycete belongs to the genus *Streptomyces*.

8. The vector of claim 5, wherein the bacterial cell other than actinomycete is *Eseherichia coli*.

9. A transformant transformed with the vector of claim 4.

10. A transformant transformed with the vector of claim 5.

11. A transformant belonging to actinomycete, which has been transformed with a vector comprising both a DNA construct comprising a first promoter that is a nitrilase gene promoter consisting of the sequence of SEQ ID NO: 15, operably linked to a structural gene and a second promoter that is a nitrilase gene promoter consisting of the sequence of SEQ ID NO: 15, wherein the second promoter is placed upstream of the nitrilase transcription regulatory protein gene from *Rhodococcus rhodochrous* J 1, and a DNA involved in a regulatory function of intracellular autonomous replication of actinomycete.

12. A transformant belonging to actinomycete, into which a DNA construct comprising a first promoter that is a nitrilase gene promoter consisting of the sequence of SEQ ID NO: 15, operably linked to a structural gene and a second promoter that is a nitrilase gene promoter consisting of the sequence of SEQ ID NO: 15, wherein the second promoter is placed upstream of the nitrilase transcription regulatory protein gene from *Rhodococcus rhodochrous* J 1, has been introduced.

13. A structural gene expression system which comprises expression of a vector comprising both a DNA construct comprising a first promoter that is a nitrilase gene promoter consisting of the sequence of SEQ ID NO: 15, operably linked to the structural gene and a second promoter that is a nitrilase gene promoter consisting of the sequence of SEQ ID NO: 15, wherein the second promoter is placed upstream of the nitrilase transcription regulatory protein gene from *Rhodococcus rhodochrous* J 1 and a DNA involved in a regulatory function of intracellular autonomous replication of actinomycete, under the control of an inducer in an actinomycete host.

14. A structural gene expression system which comprises expression of the structural gene in an actinomycete host, into which a DNA construct comprising a first promoter that is a nitrilase gene promoter consisting of the sequence of SEQ ID NO: 15, operably linked to the structural gene and a second promoter that is a nitrilase gene promoter consisting of the sequence of SEQ ID NO: 15, wherein the second promoter is placed upstream of the nitrilase transcription regulatory protein gene from *Rhodococcus rhodochrous* J 1, has been introduced, under the control of an inducer.

15. A production method of a gene product encoded by a structural gene, which comprises expression of a vector comprising both a DNA construct comprising a first promoter that is a nitrilase gene promoter consisting of the sequence of SEQ ID NO: 15, operably linked to the structural gene and a second promoter that is a nitrilase gene promoter consisting of the sequence of SEQ ID NO: 15, wherein the second promoter is placed upstream of the nitrilase transcription regulatory protein gene from *Rhodococcus rhodochrous* J 1 and a DNA involved in a regulatory function of intracellular autonomous replication of actinomycete, in an actinomycete under the control of an inducer.

16. A production method of a gene product encoded by a structural gene, which comprises expression, under the control of an inducer, of the structural gene in a host belonging to actinomycete into which a DNA construct comprising a first promoter that is a nitrilase gene promoter consisting of the sequence of SEQ ID NO: 15, operably linked to the structural gene and a second promoter that is a nitrilase gene promoter consisting of the sequence of SEQ ID NO: 15, wherein the second promoter is placed upstream of the nitrilase transcription regulatory protein gene from *Rhodococcus rhodochrous* J 1, has been introduced.

17. The DNA construct of claim 2, further comprising a terminator region upstream of the first promoter and/or the second promoter.

18. A vector comprising both the DNA construct of claim 2, and a DNA involved in a regulatory function of intracellular autonomous replication of actinomycete.

19. The vector of claim 18, further comprising a DNA involved in a regulatory function of intracellular autonomous replication of a bacterial cell other than actinomycete.

20. The vector of claim 18, wherein the actinomycete belongs to a genus other than the genus *Rhodococcus*.

21. The vector of claim 18, wherein the actinomycete belongs to the genus *Streptomyces*.

22. The vector of claim 19, wherein the bacterial cell other than actinomycete is *Escherichia coli*.

23. A transformant transformed with the vector of claim 18.

24. A transformant transformed with the vector of claim 19.

25. The transformant of claim 11, wherein the structural gene is a nitrilase gene.

26. The transformant of claim 12, wherein the structural gene is a nitrilase gene.

27. The system of claim 13, wherein the structural gene is a nitrilase gene.

28. The system of claim 14, wherein the structural gene is a nitrilase gene.

29. The production method of claim 15, wherein the structural gene is a nitrilase gene.

30. The system of claim 13, wherein the actinomycete belongs to the genus *Streptomyces*.

31. The system of claim 14, wherein the actinomycete belongs to the genus *Streptomyces*.

32. The method of claim 15, wherein the actinomycete belongs to the genus *Streptomyces*.

33. The method of claim 16, wherein the actinomycete belongs to the genus *Streptomyces*.

* * * * *